US007928087B2

(12) United States Patent
Fack et al.

(10) Patent No.: US 7,928,087 B2
(45) Date of Patent: *Apr. 19, 2011

(54) COSMETIC COMPOSITIONS CONTAINING FRUCTAN AND A CATIONIC POLYMER AND THEIR USES

(75) Inventors: Géraldine Fack, Levallois-Perret (FR); Chrystel Pourille-Grethen, Clichy (FR); Serge Restle, Saint-Prix (FR)

(73) Assignee: L'Oreal (FR)

( * ) Notice: Subject to any disclaimer, the term of this patent is extended or adjusted under 35 U.S.C. 154(b) by 1391 days.

This patent is subject to a terminal disclaimer.

(21) Appl. No.: 10/466,138

(22) PCT Filed: Jan. 11, 2002

(86) PCT No.: PCT/FR02/00108
§ 371 (c)(1),
(2), (4) Date: Dec. 29, 2003

(87) PCT Pub. No.: WO02/055036
PCT Pub. Date: Jul. 18, 2002

(65) Prior Publication Data
US 2004/0105832 A1 Jun. 3, 2004

(30) Foreign Application Priority Data
Jan. 12, 2001 (FR) .................. 01 00410

(51) Int. Cl.
*A01N 43/04* (2006.01)
*A61K 31/715* (2006.01)
*A61K 8/73* (2006.01)
(52) U.S. Cl. .................. 514/54; 514/57; 424/70.13
(58) Field of Classification Search ............. 424/69–74; 514/54, 57
See application file for complete search history.

(56) References Cited

U.S. PATENT DOCUMENTS

| 2,261,002 | A | 10/1941 | Ritter |
| 2,271,378 | A | 1/1942 | Searle |
| 2,273,780 | A | 2/1942 | Dittmar |
| 2,338,614 | A | 6/1942 | Aklin |
| 2,375,853 | A | 5/1945 | Kirby et al. |
| 2,454,547 | A | 10/1946 | Bock et al. |
| 2,528,378 | A | 10/1950 | Mannheimer |
| 2,781,354 | A | 2/1957 | Mannheimer |
| 2,961,347 | A | 11/1960 | Floyd et al. |
| 3,206,462 | A | 9/1965 | McCarty |
| 3,227,615 | A | 1/1966 | Korden et al. |
| 3,589,578 | A | 6/1971 | Kamphausen |
| 3,874,870 | A | 4/1975 | Green et al. |
| 3,929,990 | A | 12/1975 | Green et al. |
| 3,966,904 | A | 6/1976 | Green et al. |
| 4,001,432 | A | 1/1977 | Green et al. |
| 4,005,193 | A | 1/1977 | Green et al. |
| 4,025,617 | A | 5/1977 | Green et al. |
| 4,025,627 | A | 5/1977 | Green et al. |
| 4,025,653 | A | 5/1977 | Green et al. |
| 4,026,945 | A | 5/1977 | Green et al. |
| 4,027,020 | A | 5/1977 | Green et al. |
| 4,031,307 | A | 6/1977 | DeMartino et al. |
| 4,131,576 | A | 12/1978 | Iovine et al. |
| 4,693,935 | A | 9/1987 | Mazurek |
| 4,728,571 | A | 3/1988 | Clemens et al. |
| 4,820,308 | A * | 4/1989 | Madrange et al. ............... 8/405 |
| 4,820,447 | A * | 4/1989 | Medcalf et al. ............... 510/151 |
| 4,957,732 | A | 9/1990 | Grollier et al. |
| 4,972,037 | A | 11/1990 | Garbe et al. |
| 5,753,266 | A * | 5/1998 | Youssefyeh et al. .......... 424/484 |
| 6,277,893 | B1 | 8/2001 | Babenko |
| 6,685,952 | B1 * | 2/2004 | Ma et al. ....................... 424/401 |
| 2001/0022967 | A1 * | 9/2001 | Brandt et al. ............... 424/70.13 |
| 2003/0175230 | A1 * | 9/2003 | Dubief ....................... 424/70.13 |

FOREIGN PATENT DOCUMENTS

| EP | 0 342 834 | 11/1989 |
| EP | 0 412 704 A2 | 2/1991 |
| EP | 0 412 707 | 2/1991 |
| EP | 0 122 324 B2 | 2/1993 |
| EP | 0640105 | 11/1993 |
| EP | 0 337 354 B1 | 2/1994 |
| EP | 0 640 105 | 3/1995 |
| EP | 1 174 118 A1 | 6/2000 |
| EP | 0 582 152 B1 | 4/2003 |
| EP | 0 809 976 B1 | 5/2003 |
| FR | 1 583 363 | 10/1969 |
| FR | 2 080 759 | 2/1971 |
| FR | 2 162 025 | 7/1973 |
| FR | 2 320 330 | 1/1975 |
| FR | 2 252 840 | 6/1975 |
| FR | 2270846 | 12/1975 |
| FR | 2280361 | 2/1976 |
| FR | 2 316 271 | 7/1976 |
| FR | 2 368 508 | 3/1977 |
| FR | 2470596 | 6/1981 |
| FR | 2505348 | 11/1982 |
| FR | 2519863 | 7/1983 |
| FR | 2542997 | 9/1984 |
| FR | 2598611 | 11/1987 |
| FR | 2795953 | 1/2001 |
| FR | 2838660 | 10/2003 |
| WO | WO-93/23009 | 11/1993 |
| WO | WO-95/00578 | 1/1995 |
| WO | WO-98/05793 | 2/1998 |
| WO | WO-98/14482 | 4/1998 |

OTHER PUBLICATIONS

Todd & Byers, "Volatile Silicone Fluids for Cosmetics," Cosmetics and Toiletries vol. 91, Jan. 1976.

* cited by examiner

*Primary Examiner* — Sreeni Padmanabhan
*Assistant Examiner* — Kendra D Carter
(74) *Attorney, Agent, or Firm* — Lerner, David, Littenberg, Krumholz & Mentlik, LLP

(57) ABSTRACT

The invention concerns novel cosmetic compositions comprising in a cosmetically acceptable medium, at least a fructan, at least a cationic polymer. Said composition provides a flow texture to cosmetic compositions, said compositions are easily rinsed. Hair treated with said composition have a soft feel free of residue. Said compositions are used for washing and/or conditioning keratinous matter such as hair or skin.

26 Claims, No Drawings

COSMETIC COMPOSITIONS CONTAINING FRUCTAN AND A CATIONIC POLYMER AND THEIR USES

The present invention relates to novel cosmetic compositions comprising, in a cosmetically acceptable medium, at least one cationic polymer and at least one fructan.

It is well known that hair which has been sensitized (i.e. damaged and/or made fragile) to various degrees under the action of atmospheric agents or under the action of mechanical or chemical treatments, such as dyeing, bleaching and/or permanent waving, is often difficult to disentangle and to style, and lacks softness.

Combinations of polymers with thickening properties have already been proposed for the treatment of keratinous materials, and in particular of hair. Among these, combinations of polysaccharides such as inulin and acrylic terpolymers with a urethane unit have been described.

Such combinations exhibit, however, disadvantages such as the problems of rinsability, problems of stability at acidic pH, difficulties of distribution over keratinous materials and inadequate cosmetic properties.

The use of cationic polymers to facilitate the disentanglement of the hair and to impart softness and suppleness to it has already been recommended in compositions for the washing or care of keratinous materials such as the hair. The use of cationic polymers for this purpose exhibits various disadvantages. Because of their high affinity for the hair, some of these polymers become substantially deposited during repeated use, leading to undesirable effects such as a charged, unpleasant feel, a stiffening of the hair, and an interfiber adhesion affecting hair styling.

In summary, it is found that current cosmetic compositions containing cationic polymers are not completely satisfactory.

The Applicant has now discovered that the combination of a fructan with cationic polymers makes it possible to overcome these disadvantages.

Thus, following major research studies carried out on the subject, it has now been found by the Applicant that by introducing a fructan into the compositions, in particular hair compositions of the prior art based on cationic polymers, it is possible to limit, or even eliminate, the problems mentioned above.

Furthermore, this combination imparts a melting texture on the cosmetic compositions, that is to say that it rapidly disappears in the hair. Hair treated with this composition has a soft feel and no residues.

Moreover, the compositions of the invention, when applied to the skin, in particular in foam bath or shower gel form, provide an improvement in the softness of the skin.

Thus, according to the present invention, novel cosmetic compositions are now provided, comprising, in a cosmetically acceptable medium, at least one cationic polymer and at least one fructan.

Another subject of the invention relates to the use of a fructan in, or for the manufacture of a cosmetic composition comprising a cationic polymer.

The different subjects of the invention will now be presented in detail. All the meanings and definitions of the compounds used in the present invention which are given below are valid for all the subjects of the invention.

Fructans or fructosans are oligosaccharides or polysaccharides comprising a succession of anhydrofructose units optionally combined with one [lacuna] more saccharide residues different from fructose. Fructans may be linear or branched. Fructans may be products obtained directly from a plant or microbial source or alternatively products whose chain length has been modified (increased or decreased) by fractionation, synthesis or hydrolysis, in particular enzymatic hydrolysis. Fructans generally have a degree of polymerization of 2 to about 1 000, and preferably 3 to about 60.

There are 3 groups of fructans. The first group corresponds to products whose fructose units are for the majority linked by β-2-1 bonds. They are essentially linear fructans such as inulins.

The second group also corresponds to linear fructoses, but the fructose units are essentially linked by β-2-6 bonds. These products are levans.

The third group corresponds to mixed frucans, that is to say having β-2-6 and β-2-1 linkages. They are essentially branched fructans such as graminans.

The preferred fructans are inulins. Inulin may be obtained, for example, from chicory, dahlia and Jerusalem artichokes.

Preferably, the fructans according to the invention do not contain an amine group, and/or are not modified by an alkylene oxide and/or by an alkylating agent.

According to the invention, amine group denotes any group containing at least one primary, secondary or tertiary amine or a quaternary ammonium group.

As fructans are not modified by an alkylene oxide and/or by an alkylating agent, they do not therefore contain an oxyalkylenated group and/or an alkyl group.

The fructan is preferably used in a quantity of between 0.01 and 20% by weight relative to the total weight of the composition. More preferably, this quantity is between 0.05 and 15% by weight relative to the total weight of the composition, and more preferably still between 0.1 and 10% by weight.

The cationic polymers which can be used in accordance with the present invention may be chosen from all those already known per se to improve the cosmetic properties of hair, namely in particular those described in patent applications EP-A-0,337,354 and in French patent applications FR-A-2,270,846, 2,383,660, 2,598,611, 2,470,596 and 2,519,863.

Still more generally, for the purposes of the present invention, the expression "cationic polymer" denotes any polymer containing cationic groups and/or groups ionizable into cationic groups.

The preferred cationic polymers are chosen from those which contain units comprising primary, secondary, tertiary and/or quaternary amine groups which may either form part of the principal polymer chain, or which may be carried by a side substituent directly linked thereto.

The cationic polymers used generally have a number-average molecular mass of between 500 and $5 \times 10^6$ approximately, and preferably of between $10^3$ and $3 \times 10^6$ approximately.

Among the cationic polymers, there may be mentioned more particularly the polymers of the polyamine, polyamidoamide and quaternary polyammonium type. They are known products.

The polymers of the polyamine, polyamidoamide and quaternary polyammonium type which can be used in accordance with the present invention, which may be especially mentioned, are those described in French Pat. No. 2,505,348 or 2,542,997. Among these polymers, there may be mentioned:

(1) the homopolymers or copolymers derived from acrylic or methacrylic esters or amides and comprising at least one of the units of the following formulae:

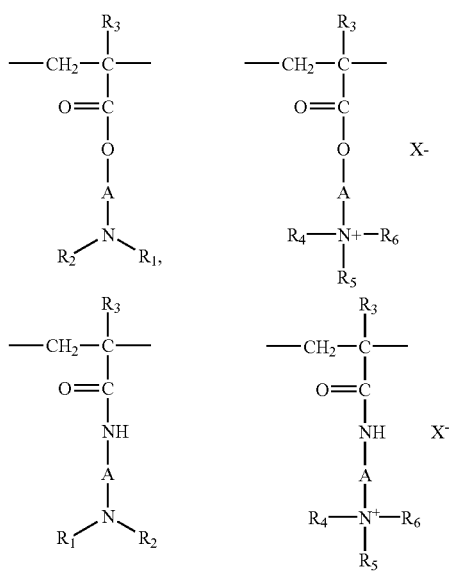

in which:
R₃, which are identical or different, denote a hydrogen atom or a CH₃ radical;
A, which are identical or different, represent a linear or branched alkyl group of 1 to 6 carbon atoms, preferably 2 or 3 carbon atoms or a hydroxyalkyl group of 1 to 4 carbon atoms;
R₄, R₅, R₆, which are identical or different, represent an alkyl group having from 1 to 18 carbon atoms or a benzyl radical and preferably an alkyl group having from 1 to 6 carbon atoms;
R₁ and R₂, which are identical or different, represent hydrogen or an alkyl group having from 1 to 6 carbon atoms and preferably methyl or ethyl;
X denotes an anion derived from an inorganic or organic acid such as a methosulfate anion or a halide such as chloride or bromide.

The copolymers of the family (1) may contain, in addition, one or more units derived from comonomers which may be chosen from the family of acrylamides, methacrylamides, diacetone acrylamides, acrylamides and methacrylamides substituted on the nitrogen with lower ($C_1$-$C_4$)alkyls, acrylic or methacrylic acids or esters thereof, vinyllactams such as vinylpyrrolidone or vinylcaprolactam, vinyl esters.

Thus, among these copolymers of the family (1), there may be mentioned:
the copolymers of acrylamide and dimethylaminoethyl methacrylate quaternized with dimethyl sulfate or with a dimethyl halide such as that sold under the name HERCOFLOC by the company HERCULES,
the copolymers of acrylamide and methacryloyloxy-ethyl-trimethylammonium chloride described, for example, in Patent Application EP-A-080976 and sold under the name BINA QUAT P 100 by the company CIBA GEIGY,
the copolymer of acrylamide and methacryloyloxy-ethyl-trimethylammonium methosulfate sold under the name RETEN by the company HERCULES,
the vinylpyrrolidone/dialkylaminoalkyl acrylate or methacrylate copolymers, quaternized or otherwise, such as the products sold under the name "GAFQUAT" by the company ISP such as for example "GAFQUAT 734" or "GAFQUAT 755" or alternatively the products called "COPOLYMER 845, 958 and 937". These polymers are described in detail in French Patents 2,077,143 and 2,393,573,
the dimethylaminoethyl methacrylate/vinylcapro-lactam/vinylpyrrolidone terpolymers such as the product sold under the name GAFFIX VC 713 by the company ISP,
the vinylpyrrolidone/methacrylamidopropyldimethylamine copolymers marketed in particular under the name STYLEZE CC 10 by ISP,
and the quaternized vinylpyrrolidone/dimethyl-aminopropyl methacrylamide copolymers such as the product sold under the name "GAFQUAT HS 100" by the company ISP.

(2) The cellulose ether derivatives comprising quaternary ammonium groups described in French Patent 1,492,597, and in particular the polymers marketed under the names "JR" (JR 400, JR 125, JR 30M) or "LR" (LR 400, LR 30M) by the company Union Carbide Corporation. These polymers are also defined in the CTFA dictionary as hydroxyethyl cellulose quaternary ammoniums which have reacted with an epoxide substituted by a trimethyl-ammonium group.

(3) Cationic cellulose derivatives such as cellulose copolymers or cellulose derivatives grafted with a quaternary ammonium water-soluble monomer, are described especially in U.S. Pat. No. 4,131,576, such as hydroxyalkyl celluloses like hydroxymethyl, hydroxyethyl or hydroxypropyl celluloses grafted especially with a methacryloylethyltrimethylammonium, methacrylamido-propyltrimethylammonium or dimethyldiallylammonium salt.
The commercialized products corresponding to this definition are more particularly the products sold under the name "Celquat L 200" and "Celquat H 100" by the company National Starch.

(4) Cationic polysaccharides described more particularly in U.S. Pat. Nos. 3,589,578 and 4,031,307 such as the guar gums containing cationic trialkylammonium groups. Guar gums modified with a 2,3-epoxypropyltrimethylammonium salt (e.g. chloride) are for example used.
Such products are marketed in particular under the trade names JAGUAR C13 S, JAGUAR C 15, JAGUAR C 17 or JAGUAR C162 by the company MEYHALL.

(5) Polymers consisting of piperazinyl units and of alkylene or hydroxyalkylene divalent radicals with straight or branched chains, optionally interrupted by oxygen, sulfur or nitrogen atoms or by aromatic or heterocyclic rings, as well as the oxidation and/or quaternization products of these polymers. Such polymers are described especially in French patents 2,162,025 and 2,280,361;

(6) Water-soluble polyaminoamides prepared in particular by polycondensation of an acid compound with a polyamine; these polyaminoamides may be crosslinked with an epihalohydrin, a diepoxide, a dianhydride, an unsaturated dianhydride, a diunsaturated derivative, a bishalohydrin, a bisazetidinium, a bishaloacyldiamine, an alkylbishalide or else with an oligomer resulting from the reaction of a difunctional compound which is reactive toward a bishalohydrin, a bisazetidinium, a bishaloacyldiamine, an alkylbishalide, an epihalohydrin, a diepoxide or a diunsaturated derivative; the crosslinking agent being employed in proportions ranging from 0.025 to 0.35 mol per amine group of the polyaminoamide; these polyaminoamides may be alkylated or, if they include one or more tertiary amine functional groups, quaternized. Such polymers are described especially in French Patents 2,252,840 and 2,368,508.

(7) Polyaminoamide derivatives resulting from the condensation of polyalkylenepolyamines with polycarboxylic acids, followed by an alkylation with bifunctional agents. There may be mentioned, for example, the adipic acid-dialkylaminohydroxy-alkyldialkylenetriamine polymers in which the alkyl radical contains from 1 to 4 carbon atoms and preferably denotes methyl, ethyl or propyl. Such polymers are described especially in French Patent 1,583,363.

Among these derivatives there may be mentioned more particularly the adipic acid/dimethyl-aminohydroxypropyl/diethylenetriamine polymers sold under the name "Cartaretine F, F4 or F8" by the company Sandoz.

(8) Polymers obtained by reaction of a polyalkylenepolyamine containing two primary amine groups and at least one secondary amine group with a dicarboxylic acid chosen from diglycolic acid and saturated aliphatic dicarboxylic acids containing from 3 to 8 carbon atoms. The molar ratio of the polyalkylenepolyamine to the dicarboxylic acid being between 0.8:1 and 1.4:1; the polyaminoamide resulting therefrom being made to react with epichlorohydrin in a molar ratio of epichlorohydrin relative to the secondary amine group of the polyaminoamide of between 0.5:1 and 1.8:1. Such polymers are described especially in U.S. Pat. Nos. 3,227,615 and 2,961,347.

Polymers of this type are marketed in particular under the name "Hercosett 57" by the company Hercules Inc. or else under the name of "PD 170" or "Delsette 101" by the company Hercules in the case of the copolymer of adipic acid/epoxypropyl/diethyl-triamine.

(9) Cyclopolymers of alkyldiallylamine or of dialkyldiallylammonium, such as the homopolymers or copolymers comprising, as main constituent of the chain, units corresponding to the formulae (VI) or (VI'):

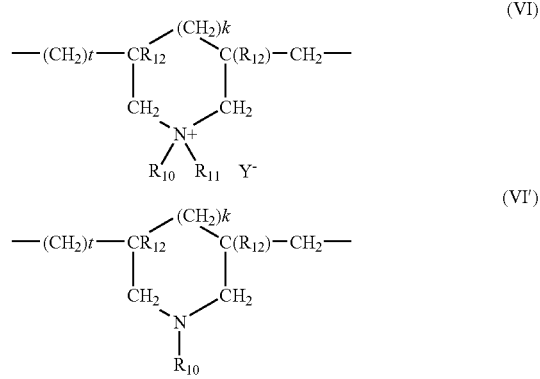

in which formulae k and t are equal to 0 or 1, the sum k+t being equal to 1; $R_{12}$ denotes a hydrogen atom or a methyl radical; $R_{10}$ and $R_{11}$, independently of each other, denote an alkyl group containing from 1 to 22 carbon atoms, a hydroxyalkyl group in which the alkyl group preferably has 1 to 5 carbon atoms, or a lower ($C_1$-$C_4$)amidoalkyl group or $R_{10}$ and $R_{11}$ may denote, jointly with the nitrogen atom to which they are attached, heterocyclic groups such as piperidinyl or morpholinyl; $Y^-$ is an anion such as bromide, chloride, acetate, borate, citrate, tartrate, bisulfate, bisulfite, sulfate or phosphate. These polymers are described especially in French Patent 2,080,759 and in its certificate of addition 2,190,406.

$R_{10}$ and $R_{11}$, independently of each other, preferably denote an alkyl group having from 1 to 4 carbon atoms.

Among the polymers defined above there may be mentioned more particularly the dimethyldiallylammonium chloride homopolymer sold under the name "Merquat 100" by the company Calgon (and its homologs of low weight-average molecular masses) and the copolymers of diallyl-dimethylammonium chloride and acrylamide marketed under the name "MERQUAT 550".

(10) The quaternary diammonium polymer containing repeat units corresponding to the formula:

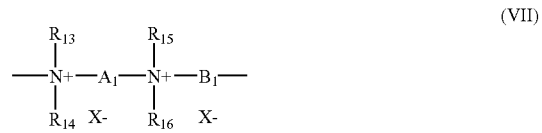

formula (VII) in which:

$R_{13}$, $R_{14}$, $R_{15}$ and $R_{16}$, which are identical or different, represent aliphatic, alicyclic or arylaliphatic radicals containing from 1 to 20 carbon atoms or lower hydroxyalkyl aliphatic radicals, or else $R_{13}$, $R_{14}$, $R_{15}$ and $R_{16}$, together or separately, form, with the nitrogen atoms to which they are attached, heterocyclic rings optionally containing a second heteroatom other than nitrogen, or else $R_{13}$, $R_{14}$, $R_{15}$ and $R_{16}$ represent a linear or branched $C_1$-$C_6$ alkyl radical substituted by a nitrile, ester, acyl, amide or —CO—O—$R_{17}$-D or —CO—NH—$R_{17}$-D group where $R_{17}$ is an alkylene and D a quaternary ammonium group;

$A_1$ and $B_1$ represent polymethylene groups containing from 2 to 20 carbon atoms which may be linear or branched, saturated or unsaturated and which may contain, bonded to or inserted into the main chain, one or more aromatic rings, or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

$A_1$, $R_{13}$ and $R_{15}$, with the two nitrogen atoms to which they are attached, may form a piperazine ring; in addition if $A_1$ denotes a saturated or unsaturated, linear or branched alkylene or hydroxyalkylene radical, $B_1$ may also denote a group $(CH_2)_n$—CO-D-OC—$(CH_2)_n$— in which D denotes:

a) a glycol residue of formula: —O—Z—O—, where Z denotes a linear or branched hydrocarbon radical or a group corresponding to one of the following formulae:

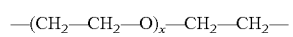

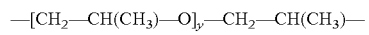

where x and y denote an integer from 1 to 4, representing a defined and unique degree of polymerization or any number from 1 to 4 representing a mean degree of polymerization;

b) a disecondary diamine residue such as a piperazine derivative;

c) a diprimary diamine residue of formula: —NH—Y—NH—, where Y denotes a linear or branched hydrocarbon radical or else the divalent radical

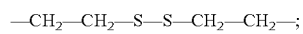

d) a ureylene group of formula: —NH—CO—NH—;

$X^-$ is preferably an anion such as chloride or bromide.

These polymers have a number-average molecular mass which is generally between 1000 and 100,000.

Polymers of this type are described especially in French Patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is possible to use more particularly the polymers which consist of repeat units corresponding to the formula:

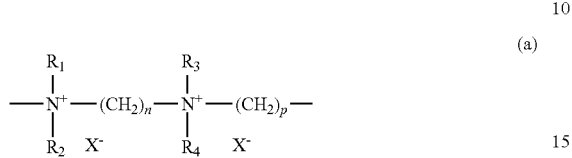

in which $R_1$, $R_2$, $R_3$ and $R_4$, which are identical or different, denote an alkyl or hydroxyalkyl radical having from 1 to 4 carbon atoms approximately, n and p are integers varying from 2 to 20 approximately and $X^-$ is an anion derived from an inorganic or organic acid.

An especially preferred compound of formula (a) is that for which $R_1$, $R_2$, $R_3$ and $R_4$ represent a methyl radical and n=3, p=6 and X=Cl, called Hexadimethrine chloride according to the INCI nomenclature (CTFA).

(11) Quaternary polyammonium polymers consisting of units of formula (VIII):

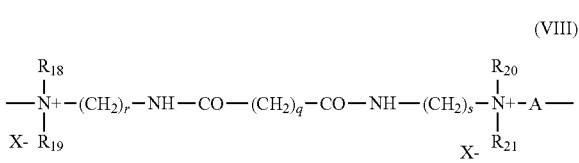

in which formula:

$R_{18}$, $R_{19}$, $R_{20}$ and $R_{21}$, which are identical or different, represent a hydrogen atom or a methyl, ethyl, propyl, β-hydroxyethyl, β-hydroxypropyl or $-CH_2CH_2(OCH_2CH_2)_p$ OH radical, where p is equal to 0 or to an integer between 1 and 6, provided that $R_{18}$, $R_{19}$, $R_{20}$ and $R_{21}$ do not simultaneously denote a hydrogen atom, r and s, which are identical or different, are integers between 1 and 6, q is equal to 0 or to an integer between 1 and 34, $X^-$ denotes an anion such as a halide, A denotes a radical of a dihalide or preferably represents $-CH_2-CH_2-O-CH_2-CH_2-$.

Such compounds are described especially in Patent Application EP-A-122 324.

Among these there may be mentioned, for example, the products "Mirapol® A 15", "Mirapol® AD1", "Mirapol® AZ1" and "Mirapol® 175", sold by the company Miranol.

(12) Quaternary vinylpyrrolidone and vinylimidazole polymers such as, for example, the products marketed under the names Luviquat® FC 905, FC 550 and FC 370 by the company B.A.S.F.

(13) Polyamines like the Polyquart® H sold by HENKEL, referred to under the name of "Polyethylene glycol (15) Tallow Polyamine" in the CTFA dictionary.

(14) The crosslinked polymers of methacryloyloxy($C_1$-$C_4$ alkyl)tri($C_1$-$C_4$ alkyl)ammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. More particularly, it is possible to employ a crosslinked acrylamide/methacryloyloxyethyltrimethylammonium chloride copolymer (20/80 by weight) in the form of a dispersion containing 50% by weight of said copolymer in mineral oil. This dispersion is marketed under the name of "SALCARE® SC 92" by the company ALLIED COLLOIDS. It is also possible to employ a crosslinked methacryloyloxyethyltrimethylammonium chloride homopolymer containing approximately 50% by weight of the homopolymer in mineral oil or in a liquid ester. These dispersions are marketed under the names of "SALCARE® SC 95" and "SALCARE® SC 96" by the company ALLIED COLLOIDS.

Other cationic polymers that may be employed within the scope of the invention are cationic proteins or hydrolysates of cationic proteins, polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers capable of being used within the scope of the present invention, it is preferable to use quaternary cellulose ether derivatives such as the products sold under the name "JR 400" by the company UNION CARBIDE CORPORATION, cationic cyclopolymers, in particular the homopolymers or copolymers of dimethyldiallylammonium chloride, sold under the names "MERQUAT 100", "MERQUAT 550" and "MERQUAT S" by the company CALGON, quaternary vinylpyrrolidone and vinylimidazole polymers, the crosslinked homopolymers or copolymers of methacryloyloxy($C_1$-$C_4$)alkyl($C_1$-$C_4$)trialkylammonium salts and mixtures thereof.

According to the invention, the cationic polymer(s) may represent from 0.001% to 20% by weight, preferably from 0.01% to 10% by weight, and more particularly from 0.1 to 5% by weight relative to the total weight of the final composition.

According to a particularly preferred embodiment, the compositions according to the invention comprise, in addition, at least one silicone or another agent which is beneficial to the hair, such as in particular the esters of $C_1$-$C_{30}$ carboxylic acids and of mono- or polyhydroxylated $C_1$-$C_{30}$ alcohols, vegetable, animal, mineral or synthetic oils, waxes, ceramides or pseudoceramides.

The silicones which can be used in accordance with the invention are in particular polyorganosiloxanes which are insoluble in the composition and they may be provided in the form of oils, waxes, resins or gums.

The organopolysiloxanes are defined in greater detail in the book by Walter NOLL "Chemistry and Technology of Silicones" (1968) Academic Press. They may be volatile or non-volatile.

When they are volatile, the silicones are more particularly chosen from those possessing a boiling point of between 60° C. and 260° C., and more particularly still from:

(i) cyclic silicones comprising from 3 to 7 silicon atoms, and preferably 4 to 5. They are, for example, the octamethylcyclotetrasiloxane marketed in particular under the name "VOLATILE SILICONE 7207" by UNION CARBIDE or "SILBIONE 70045 V 2" by RHONE POULENC, the decamethylcyclopentasiloxane marketed under the name "VOLATILE SILICONE 7158" by UNION CARBIDE, "SILBIONE 70045 V 5" by RHONE POULENC, and mixtures thereof.

There may also be mentioned cyclocopolymers of the dimethylsiloxane/methylalkylsiloxane type, such as the "SILICONE VOLATILE FZ 3109" marketed by the company UNION CARBIDE, having the chemical structure:

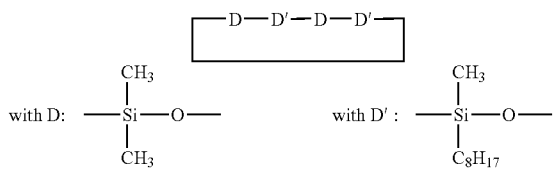

There may also be mentioned mixtures of cyclic silicones with organic compounds derived from silicon, such as the mixture of octamethylcyclotetrasiloxane and tetratrimethylsilylpentaerythritol (50/50) and the mixture of octamethylcyclotetrasiloxane and 1,1'-oxy(2,2,2',2',3,3'-hexatrimethylsilyloxy)bisneopentane;

(ii) linear volatile silicones having 2 to 9 silicon atoms and possessing a viscosity of less than or equal to $5 \times 10^{-6}$ m$^2$/s at 25° C. It is for example the decamethyltetrasiloxane marketed in particular under the name "SH 200" by the company TORAY SILICONE. Silicones entering into this class are also described in the article published in Cosmetics and toiletries, Vol. 91, Jan. 76, p. 27-32—TODD & BYERS "Volatile Silicone fluids for cosmetics".

Nonvolatile silicones and more particularly polyalkylsiloxanes, polyarylsiloxanes, polyalkylarylsiloxanes, silicone gums and resins, polyorganosiloxanes modified by organofunctional groups and mixtures thereof are preferably used.

These silicones are more particularly chosen from polyalkylsiloxanes among which there may be mentioned mainly polydimethylsiloxanes with terminal trimethylsilyl groups having a viscosity of $5 \times 10^{-6}$ to 2.5 m$^2$/s at 25° C. and preferably $1 \times 10^{-5}$ to 1 m$^2$/s. The viscosity of the silicones is, for example, measured at 25° C. according to the ASTM 445 Appendix C standard.

Among these polyalkylsiloxanes, there may be mentioned, without limitation, the following commercial products:
SILBIONE oils of the 47 and 70 047 series or MIRASIL oils marketed by RHONE POULENC such as, for example, the 70 047 V 500 000 oil;
oils of the MIRASIL series marketed by the company RHONE POULENC;
oils of the 200 series from the company DOW CORNING such as more particularly DC200 having a viscosity of 60 000 Cst;
VISCASIL oils from GENERAL ELECTRIC and certain oils of the SF series (SF 96, SF 18) from GENERAL ELECTRIC.

There may also be mentioned the polydimethylsiloxanes with terminal dimethylsilanol groups (Dimethiconol according to the CTFA name), such as the oils of the 48 series from the company RHONE POULENC.

In this class of polyalkylsiloxanes, there may also be mentioned the products marketed under the names "ABIL WAX 9800 and 9801" by the company GOLDSCHMIDT which are poly($C_1$-$C_{20}$)alkylsiloxanes.

The polyalkylarylsiloxanes are particularly chosen from polydimethyl methylphenylsiloxanes, polydimethyl diphenylsiloxanes which are linear and/or branched and have a viscosity of $1 \times 10^{-5}$ to $5 \times 10^{-2}$ m$^2$/s at 25° C.

Among these polyalkylarylsiloxanes, there may be mentioned, by way of example, the products marketed under the following names:
SILBIONE oils of the 70 641 series from RHONE POULENC;
oils of the RHODORSIL 70 633 and 763 series from RHONE POULENC;
DOW CORNING 556 COSMETIC GRAD FLUID oil from DOW CORNING;
silicones of the PK series from BAYER such as the product PK20;
silicones of the PN, PH series from BAYER such as the products PN1000 and PH1000;
certain oils of the SF series from GENERAL ELECTRIC such as SF 1023, SF 1154, SF 1250, SF 1265.

The silicone gums which can be used in accordance with the invention are in particular polydiorganosiloxanes having high number-average molecular masses of between 200,000 and 1,000,000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane, tridecane or mixtures thereof.

The following products may be more particularly mentioned:
polydimethylsiloxane,
polydimethylsiloxane/methylvinylsiloxane gums,
polydimethylsiloxane/diphenylsiloxane,
polydimethylsiloxane/phenylmethylsiloxane,
polydimethylsiloxane/diphenylsiloxane/methylvinylsiloxane.

Products which can be more particularly used in accordance with the invention are mixtures such as:
the mixtures formed from a polydimethylsiloxane hydroxylated at the chain end (called dimethiconol according to the nomenclature of the CTFA dictionary) and from a cyclic dimethylsiloxane (called cyclomethicone according to the nomenclature of the CTFA dictionary) such as the product Q2 1401 marketed by the company DOW CORNING;
the mixtures formed from a polydimethylsiloxane gum with a cyclic silicone such as the product SF 1214 Silicone Fluid from the company GENERAL ELECTRIC; this product is a gum SF 30 corresponding to a dimethicone, having a number-average molecular weight of 500 000, solubilized in the oil SF 1202 Silicone Fluid corresponding to decamethylcyclopentasiloxane;
the mixtures of two PDMSs of different viscosities, and more particularly of a PDMS gum and a PDMS oil, such as the product SF 1236 from the company GENERAL ELECTRIC. The product SF 1236 is the mixture of an SE 30 gum defined above having a viscosity of 20 m$^2$/s and an SF 96 oil having a viscosity of $5 \times 10^{-6}$ m$^2$/s. This product preferably comprises 15% of SE 30 gum and 85% of an SF 96 oil.

The organopolysiloxane resins which can be used in accordance with the invention are crosslinked siloxane systems containing the units:
$R_2SiO_{2/2}$, $R_3SiO_{1/2}$, $RSiO_{3/2}$ and $SiO_{4/2}$ in which R represents a hydrocarbon group possessing 1 to 16 carbon atoms or a phenyl group. Among these products, those particularly preferred are those in which R denotes a $C_1$-$C_4$ lower alkyl, more particularly methyl, radical or a phenyl radical.

There may be mentioned among these resins the product marketed under the name "DOW CORNING 593" or those marketed under the names "SILICONE FLUID SS 4230 and SS 4267" by the company GENERAL ELECTRIC and which are silicones having the dimethyl/trimethylsiloxane structure.

There may also be mentioned the resins of the trimethylsilyloxysilicate type which are marketed in particular under the names X22-4914, X21-5034 and X21-5037 by the company SHIN-ETSU.

The organomodified silicones which can be used in accordance with the invention are silicones as defined above and comprising in their structure one or more organofunctional groups attached via a hydrocarbon group.

Among the organomodified silicones, there may be mentioned the polyorganosiloxanes comprising:

polyethyleneoxy and/or polypropyleneoxy groups optionally comprising $C_6$-$C_{24}$ alkyl groups such as the products called dimethicone-copolyol marketed by the company DOW CORNING under the name DC 1248 or the oils SILWET® L 722, L 7500, L 77, L 711 from the company UNION CARBIDE and the ($C_{12}$)alkyl methicone-copolyol marketed by the company DOW CORNING under the name Q2 5200;

substituted or unsubstituted amine-containing groups such as the products marketed under the name GP 4 Silicone Fluid and GP 7100 by the company GENESEE or the products marketed under the names Q2 8220 and DOW CORNING 929 or 939 by the company DOW CORNING. The substituted amine-containing groups are in particular $C_1$-$C_4$ aminoalkyl groups;

thiol groups, such as the products marketed under the names "GP 72 A" and "GP 71" from GENESEE;

alkoxylated groups, such as the product marketed under the name "SILICONE COPOLYMER F-755" by SWS SILICONES and ABIL WAX 2428, 2434 and 2440 by the company GOLDSCHMIDT;

hydroxylated groups, such as the polyorganosiloxanes with a hydroxyalkyl functional group which are described in French patent application FR-A-85 16334 corresponding to the formula (IX):

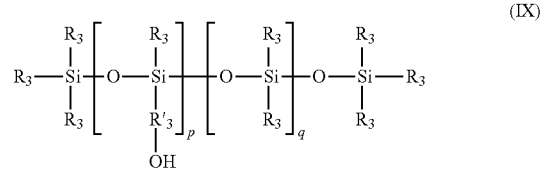
(IX)

in which the $R_3$ radicals, which are identical or different, are chosen from methyl and phenyl radicals; at least 60 mol % of the $R_3$ radicals denoting methyl; the R'$_3$ radical is a divalent hydrocarbon $C_2$-$C_{18}$ alkylene member; p is between 1 and 30 inclusive; q is between 1 and 150 inclusive;

acyloxyalkyl groups such as, for example, the polyorganosiloxanes described in patent U.S. Pat. No. 4,957,732 and corresponding to the formula (X):

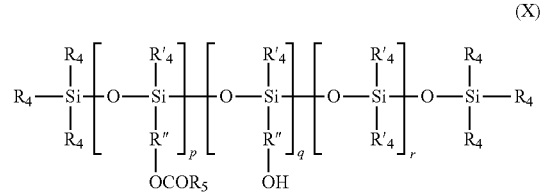
(X)

in which:
$R_4$ denotes a methyl, phenyl, —OCOR$_5$ or hydroxyl group, it being possible for only one of these $R_4$ radicals per silicon atom to be OH;
R'$_4$ denotes methyl or phenyl; at least 60%, as a molar proportion, of all the $R_4$ and R'$_4$ radicals denoting methyl;
$R_5$ denotes a $C_8$-$C_{20}$ alkyl or alkenyl;
R" denotes a linear or branched, divalent hydrocarbon $C_2$-$C_{18}$ alkylene radical;
r is between 1 and 120 inclusive;
p is between 1 and 30;
q is equal to 0 or is less than 0.5 p, p+q being between 1 and 30; the polyorganosiloxanes of formula (VI) may contain groups:

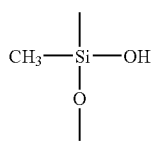

in proportions not exceeding 15% of the sum p+q+r;
anionic groups of the carboxylic type, such as, for example, in the products described in patent EP 186 507 from the company CHISSO CORPORATION, or of the alkylcarboxylic type such as those present in the product X-22-3701E from the company SHIN-ETSU; 2-hydroxyalkylsulfonate; 2-hydroxyalkylthiosulfate such as the products marketed by the company GOLDSCHMIDT under the names "ABIL S201" and "ABIL S255";
hydroxyacylamino groups, such as the polyorganosiloxanes described in application EP 342 834. There may be mentioned, for example, the product Q2-8413 from the company DOW CORNING.

According to the invention, it is also possible to use silicones comprising a polysiloxane portion and a portion consisting of a nonsilicone organic chain, one of the two portions constituting the principal chain of the polymer, the other being grafted onto said principal chain. These polymers are for example described in patent applications EP-A-412 704, EP-A-412 707, EP-A-640 105 and WO 95/00578, EP-A-582 152 and WO 93/23009 and patents U.S. Pat. Nos. 4,693,935, 4,728,571 and 4,972,037. These polymers are preferably anionic or nonionic.

Such polymers are, for example, the polymers which can be obtained by free-radical polymerization starting with a mixture of monomers, consisting of:
a) 50 to 90% by weight of tert-butyl acrylate;
b) 0 to 40% by weight of acrylic acid;
c) 5 to 40% by weight of silicone-containing macromer of formula:

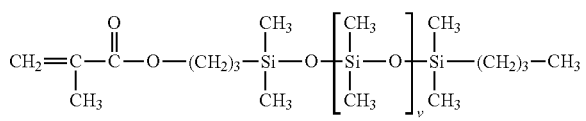

with v being a number ranging from 5 to 700; the percentages by weight being calculated relative to the total weight of the monomers.

Other examples of graft silicone-containing polymers are in particular polydimethylsiloxanes (PDMS) on which are grafted, via a linking member of the thiopropylene type, mixed polymer units of the poly(meth)acrylic acid type and of the polyalkyl (meth)acrylate type, and polydimethylsiloxanes (PDMS) on which are grafted, via a linking member of the thiopropylene type, polymer units of the polyisobutyl (meth)acrylate type.

According to the invention, all the silicones may also be used in the form of emulsions, nano-emulsions or macroemulsions.

The particularly preferred polyorganosiloxanes in accordance with the invention are:

nonvolatile silicones chosen from the family of polyalkylsiloxanes with trimethylsilyl terminal groups such as oils having a viscosity of between 0.2 and 2.5 m²/s at 25° C. such as the oils of the DC200 series from DOW CORNING, in particular that of viscosity 60,000 Cst, of the series SILBIONE 70047 and 47 and more particularly the oil 70 047 V 500 000 marketed by the company RHONE POULENC, the polyalkylsiloxanes with dimethylsilanol terminal groups such as dimethiconol or the polyalkylarylsiloxanes such as the SILBIONE 70641 V 200 oil marketed by the company RHONE POULENC;

the organopolysiloxane resin marketed under the name DOW CORNING 593;

the polysiloxanes with amino groups such as amodimethicones or trimethylsilylamodimethicone.

According to the invention, the additional silicones or the other additional beneficial agents may represent from 0.001% to 20% by weight, preferably from 0.01% to 10% by weight and more particularly from 0.1 to 5% by weight relative to the total weight of the final composition.

The compositions of the invention advantageously contain, in addition, at least one surfactant which is generally present in a quantity of between 0.05% and 50% by weight approximately, preferably between 0.1% and 40% and still more preferably between 0.55% and 30%, relative to the total weight of the composition.

This surfactant may be chosen from anionic, amphoteric, nonionic and cationic surfactants, or mixtures thereof.

The surfactants which are suitable for carrying out the present invention are especially the following:

(i) Anionic Surfactant(s):

Their nature is not of truly critical importance within the context of the present invention.

Thus, by way of example of anionic surfactants that can be employed, by themselves or as mixtures, in the context of the present invention, there may be mentioned especially (nonlimiting list) the salts (in particular alkali metal, especially sodium, salts, ammonium salts, amine salts, amino alcohol salts or magnesium salts) of the following compounds: alkyl sulfates, alkyl ether sulfates, alkylamido ether sulfates, alkylaryl-polyether sulfates, monoglyceride sulfates, alkyl sulfonates, alkyl phosphates, alkylamidesulfonates, alkyl aryl sulfonates, α-olefin-sulfonates, paraffin-sulfonates, alkyl sulfosuccinates, alkyl ether sulfosuccinates, alkylamidesulfosuccinates, alkyl sulfosuccinamates, alkyl sulfoacetates, alkyl ether phosphates, acyl sarcosinates, acyl isethionates and N-acyltaurates, the alkyl or acyl radical of all these different compounds preferably containing from 8 to 24 carbon atoms, and the aryl radical preferably denoting a phenyl or benzyl group. Among the anionic surfactants which are further usable there may also be mentioned the salts of fatty acids such as the salts of oleic, ricinoleic, palmitic and stearic acids, the acids of copra oil or of hydrogenated copra oil, and acyl lactylates in which the acyl radical contains 8 to 20 carbon atoms. It is also possible to employ weakly anionic surfactants, like alkyl-D-galactosideuronic acids and salts thereof, as well as the polyoxyalkylenated carboxylic ($C_6$-$C_{24}$)alkyl ether acids, the polyoxyalkylenated carboxylic ($C_6$-$C_{24}$)alkylaryl ether acids, the polyoxyalkylenated carboxylic ($C_6$-$C_{24}$) alkyl amidoether acids and their salts, in particular those containing from 2 to 50 ethylene oxide groups and mixtures thereof.

Among the anionic surfactants, the use of the salts of alkyl sulfates and of alkyl ether sulfates and mixtures thereof is preferred according to the invention.

(ii) Nonionic Surfactant(s):

The nonionic surfactants themselves are also compounds which are well known per se (in this respect see especially the "Handbook of Surfactants" by M. R. Porter, published by Blackie & Son (Glasgow and London), 1991, pp. 116-178) and, in the context of the present invention, their nature is not of critical importance. They can thus be chosen especially from (nonlimiting list) alcohols, alpha-diols, alkylphenols or polyethoxylated, polypropoxylated or polyglycerolated fatty acids which have a fatty chain containing, for example, 8 to 18 carbon atoms, it being possible for the number of ethylene oxide or propylene oxide groups to range especially from 2 to 50 and it being possible for the number of glycerol groups to range especially from 2 to 30. The copolymers of ethylene oxide and propylene oxide and the condensates of ethylene oxide and propylene oxide with fatty alcohols may also be mentioned; the polyethoxylated fatty amides preferably containing from 2 to 30 mol of ethylene oxide, the polyglycerolated fatty amides on average containing 1 to 5 glycerol groups and in particular 1.5 to 4, the polyethoxylated fatty amines preferably containing 2 to 30 mol of ethylene oxide, the oxyethylenated fatty acid esters of sorbitan containing from 2 to 30 mol of ethylene oxide, the fatty acid esters of sucrose, the fatty acid esters of polyethylene glycol, alkylpolyglycosides, the N-alkylglucamine derivatives, amine oxides such as the oxides of ($C_{10}$-$C_{14}$) alkylamines or the N-acylaminopropylmorpholine oxides. It will be noted that alkylpolyglycosides constitute nonionic surfactants which are particularly well suited within the context of the present invention.

(iii) Amphoteric Surfactant(s):

The amphoteric surfactants, the nature of which is not of critical importance in the context of the present invention, may be especially (nonlimiting list) derivatives of aliphatic secondary or tertiary amines in which the aliphatic radical is a linear or branched chain containing 8 to 22 carbon atoms and containing at least one water-solubilizing anionic group (for example carboxylate, sulfonate, sulfate, phosphate or phosphonate); ($C_8$-$C_{20}$)alkylbetaines, sulfobetaines, ($C_8$-$C_{20}$)alkylamido ($C_1$-$C_6$)alkylbetaines or ($C_8$-$C_{20}$)alkylamido ($C_1$-$C_6$)alkylsulfobetaines may further be mentioned.

Among the amine derivatives there may be mentioned the products sold under the name MIRANOL, as described in U.S. Pat. Nos. 2,528,378 and 2,781,354 and of structures:

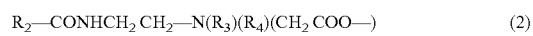

$$R_2\text{—CONHCH}_2\,CH_2\text{—N}(R_3)(R_4)(CH_2\,COO\text{—}) \qquad (2)$$

in which: $R_2$ denotes an alkyl radical derived from an acid $R_2$—COOH present in hydrolyzed copra oil, a heptyl, nonyl or undecyl radical, $R_3$ denotes a beta-hydroxyethyl group and $R_4$ a carboxymethyl group;
and

$$R_5\text{—CONHCH}_2CH_2\text{—N(B)(C)} \qquad (3)$$

in which:
B represents —$CH_2CH_2OX'$, C represents —$(CH_2)_z$—Y', with z=1 or 2,
X' denotes the —$CH_2CH_2$—COOH group or a hydrogen atom,
Y' denotes —COOH or the radical —$CH_2$—CHOH—$SO_3H$, R$_5$ denotes an alkyl radical of an acid R$_9$—COOH present in copra oil or in hydrolyzed linseed oil, an alkyl radical, especially C$_7$, C$_9$, C$_{11}$ or C$_{13}$, a C$_{17}$ alkyl radical and its iso form or an unsaturated radical C$_{17}$.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid, Cocoamphodipropionic acid.

By way of example, there may be mentioned the cocoamphodiacetate marketed under the trade name MIRANOL C2M concentrate by the company RHONE POULENC.

(iv) The cationic surfactants may be chosen from:

A) the quaternary ammonium salts of the following general formula (IV):

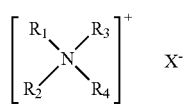

(IV)

in which X is an anion chosen from the group comprising halides (chloride, bromide or iodide) or (C$_2$-C$_6$)alkyl sulfates, more particularly methyl sulfate, phosphates, alkyl or alkylaryl sulfonates, anions derived from organic acid such as acetate or lactate, and a) the radicals R$_1$ to R$_3$, which may be identical or different, represent a linear or branched aliphatic radical comprising from 1 to 4 carbon atoms, or an aromatic radical such as alkyl or alkylaryl. The aliphatic radicals may comprise heteroatoms such as in particular oxygen, nitrogen, sulfur, halogens. The aliphatic radicals are, for example, chosen from alkyl, alkoxy and alkylamide radicals, R$_4$ denotes a linear or branched alkyl radical comprising from 16 to 30 carbon atoms.

Preferably, the cationic surfactant is a salt (for example chloride) of behenyltrimethylammonium.

b) The radicals R$_1$ and R$_2$, which may be identical or different, represent a linear or branched aliphatic radical comprising from 1 to 4 carbon atoms, or an aromatic radical such as aryl or alkylaryl. The aliphatic radicals may comprise heteroatoms such as, in particular oxygen, nitrogen, sulfur, halogens. The aliphatic radicals are, for example, chosen from alkyl, alkoxy, alkylamide and hydroxyalkyl radicals comprising about from 1 to 4 carbon atoms;

R$_3$ and R$_4$, which may be identical or different, denote a linear or branched alkyl radical comprising from 12 to 30 carbon atoms, said radical comprising at least one ester or amide functional group, R$_3$ and R$_4$ are in particular chosen from the radicals (C$_{12}$-C$_{22}$) alkylamido(C$_2$-C$_6$)alkyl, (C$_{12}$-C$_{22}$)alkyl acetate.

Preferably, the cationic surfactant is a salt (for example chloride) of stearamidopropyldimethyl-(myristylacetate)ammonium, B)—the quaternary ammonium salts of imidazolinium, such as for example that of the following formula (V):

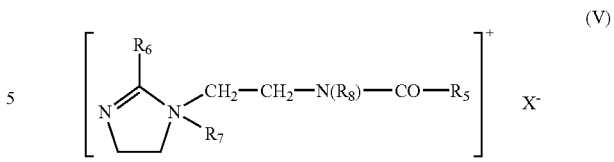

(V)

in which R$_5$ represents an alkenyl or alkyl radical comprising from 8 to 30 carbon atoms, for example derived from tallow fatty acids, R$_6$ represents a hydrogen atom, a C$_1$-C$_4$ alkyl radical or an alkenyl or alkyl radical comprising from 8 to 30 carbon atoms, R$_7$ represents a C$_1$-C$_4$ alkyl radical, R$_8$ represents a hydrogen atom, a C$_1$-C$_4$ alkyl radical, X is an anion chosen from the group comprising halides, phosphates, acetates, lactates, alkyl sulfates, alkyl or alkylaryl sulfonates. Preferably, R$_5$ and R$_6$ denote a mixture of alkenyl or alkyl radicals comprising from 12 to 21 carbon atoms, for example derived from tallow fatty acids, R$_7$ denotes methyl, R$_8$ denotes hydrogen. Such a product is, for example, Quaternium-27 (CTFA 1997) or Quaternium-83 (CTFA 1997) marketed under the names "REWOQUAT" W 75, W90, W75PG, W75HPG by the company WITCO, C)—the quaternary diammonium salts of formula (VI):

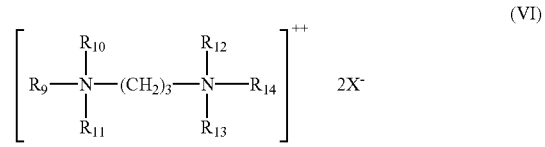

(VI)

in which Rg denotes an aliphatic radical comprising about from 16 to 30 carbon atoms, R$_{10}$, R$_{11}$, R$_{12}$, R$_{13}$, R$_{14}$, which are identical or different, are chosen from hydrogen or an alkyl radical comprising from 1 to 4 carbon atoms, and X is an anion chosen from the group comprising halides, acetates, phosphates, nitrates and methyl sulfates. Such quaternary diammonium salts optionally comprise propane tallow diammonium dichloride, D)—the quaternary ammonium salts containing at least one ester functional group of the following formula (VII):

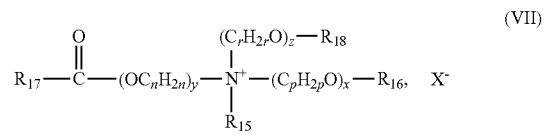

(VII)

in which:

R$_{15}$ is chosen from C$_1$-C$_6$ alkyl radicals and C$_1$-C$_6$ hydroxyalkyl or dihydroxyalkyl radicals;

R$_{16}$ is chosen from:
the radical

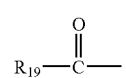

the saturated or unsaturated, linear or branched C$_1$-C$_{22}$ hydrocarbon radicals R$_{20}$,
a hydrogen atom, $R_{18}$ is chosen from:
the radical

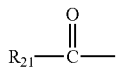

the saturated or unsaturated, linear or branched $C_7$-$C_6$ hydrocarbon radicals $R_{22}$,
a hydrogen atom,
$R_{17}$, $R_{19}$ and $R_{21}$, which are identical or different, are chosen from saturated or unsaturated, linear or branched $C_7$-$C_{21}$ hydrocarbon radicals;
n, p and r, which are identical or different, are integers ranging from 2 to 6;
y is an integer ranging from 1 to 10;
x and z, which are identical or different, are integers ranging from 0 to 10;
$X^-$ is a simple or complex, organic or inorganic anion; provided that x+y+z is equal to 1 to 15, that when x is equal to 0, then $R_{16}$ denotes $R_{20}$ and that when z is equal to 0 then $R_{18}$ denotes $R_{22}$.

There are more particularly used the ammonium salts of formula (VII) in which:
$R_{15}$ denotes a methyl or ethyl radical;
x and y are equal to 1;
z is equal to 0 or 1;
n, p and r are equal to 2;
$R_{16}$ is chosen from:
the radical

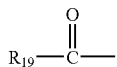

the methyl, ethyl or $C_{14}$-$C_{22}$ hydrocarbon radicals,
a hydrogen atom;
$R_{17}$, $R_{19}$ and $R_{21}$, which are identical or different, are chosen from saturated or unsaturated, linear or branched $C_7$-$C_{21}$ hydrocarbon radicals;
$R_{18}$ is chosen from:
the radical

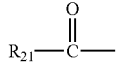

a hydrogen atom.

Such compounds are, for example, marketed under the names DEHYQUART by the company HENKEL, STEPAN-QUAT by the company STEPAN, NOXAMIUM by the company CECA, REWOQUAT WE 18 by the company REWO-WITCO.

Among the quaternary ammonium salts, there is preferred behenyltrimethylammonium chloride, or stearamidopropyldimethyl(myristylacetate)ammonium chloride marketed under the name "CERAPHYL 70" by the company VAN DYK, Quaternium-27 or Quaternium-83 marketed by the company WITCO.

In the compositions according to the invention, there may be used mixture of surfactants and in particular mixtures of anionic surfactants, mixtures of anionic surfactants and of amphoteric, cationic or nonionic surfactants, mixtures of cationic surfactants with nonionic or amphoteric surfactants. A particularly preferred mixture is a mixture consisting of at least one anionic surfactant and at least one amphoteric surfactant.

A composition of the invention may also contain at least one additive chosen from thickeners, perfumes, pearlescent agents, preservatives, sunscreens which are silicone-based or otherwise, vitamins, provitamins, anionic or nonionic polymers, noncationic proteins, noncationic protein hydrolysates, 18-methyl-eicosanoic acid, hydroxy acids, panthenol, and any other additive conventionally used in the cosmetic field which does not affect the properties of the compositions according to the invention.

These additives are optionally present in the composition according to the invention in proportions which may range from 0.001 to 20% by weight relative to the total weight of the composition. The precise quantity of each additive is easily determined by persons skilled in the art depending on its nature and its function.

The compositions in accordance with the invention may be more particularly used for washing or treating keratinous materials such as the hair, the skin, the eyelashes, the eyebrows, the nails, the lips, the scalp and more particularly the hair.

The compositions according to the invention are detergent compositions such as shampoos, shower gels and foam baths. In this embodiment of the invention, the compositions comprise at least one, generally aqueous, washing base.

The surfactant(s) constituting the washing base may equally well be chosen, alone or as mixtures, from anionic, amphoteric, nonionic and cationic surfactants as defined above.

An anionic surfactant is preferably used which is chosen from sodium, triethanolamine or ammonium ($C_{12}$-$C_{14}$)alkyl sulfates, oxyethylenated sodium, triethanolamine or ammonium ($C_{12}$-$C_{14}$)alkyl ether sulfates containing 2.2 mol of ethylene oxide, sodium cocoyl isethionate and sodium ($C_{14}$-$C_{16}$) alphaolefin sulfonate and their mixtures with:
either an amphoteric surfactant such as the amine derivatives called disodium cocoamphodipropionate or sodium cocoamphopropionate marketed in particular by the company RHONE POULENC under the trade name "MIRANOL C2M CONC" in aqueous solution at 38% of active material and under the name MIRANOL C32;
or an amphoteric surfactant of the zwitterionic type such as the alkylbetaines in particular cocobetaine marketed under the name "DEHYTON AB 30" in aqueous solution at 32% AM by the company HENKEL.

The quantity and the quality of the washing base are those sufficient to confer on the final composition a satisfactory foaming and/or detergent power.

Thus, according to the invention, the washing base may represent from 4% to 50% by weight, preferably from 6% to 35% by weight, and still more preferably from 8% to 25% by weight, of the total weight of the final composition.

The subject of the invention is also a method of treating keratinous materials such as the skin or the hair, characterized in that it consists in applying to the keratinous materials a cosmetic composition as defined above, and then in optionally rinsing with water.

Thus, this method according to the invention allows the retention of the hairstyle, the treatment, the care or the washing of or the removal of make-up from the skin, the hair or any other keratinous material.

The compositions of the invention may also be provided in the form of an after-shampoo to be rinsed off or otherwise, of compositions for permanent waving, for hair straightening, for dyeing or bleaching, or alternatively in the form of rinse-off compositions to be applied before or after dyeing, bleaching, permanent waving or hair straightening or alternatively between the two stages of a permanent waving or a hair straightening treatment.

When the composition is provided in the form of an optional rinse-off after-shampoo, it advantageously contains at least one cationic surfactant, its concentration generally being between 0.1 and 10% by weight, and preferably from 0.5 to 5% by weight relative to the total weight of the composition.

The compositions of the invention may also be provided in the form of washing compositions for the skin, and in particular in the form of bath or shower solutions or gels or of make-up removing products.

The compositions according to the invention may also be provided in the form of aqueous or aqueous-alcoholic lotions for skin and/or hair care.

The cosmetic compositions according to the invention may be provided in the form of a gel, milk, cream, emulsion, thickened lotion or foam and may be used for the skin, nails, eyelashes, lips and more particularly the hair.

The compositions may be packaged in various forms, in particular in vaporizers, pump dispensers or in aerosol containers in order to allow application of the composition in vaporized form or in foam form. Such forms of packaging are advisable, for example, when it is desired to obtain a spray, a lacquer or a foam for treating the hair.

In the text which follows or in the preceding text, the percentages expressed are by weight.

The invention will now be illustrated more fully with the aid of the following examples which should not be considered as limiting it to the embodiments described. In the examples, AS means active substance.

In the examples, trade names have the following definitions:

EXAMPLE 1

An after-shampoo in accordance with the invention was prepared which has the following composition:

| | |
|---|---|
| Inulin (RAFTILINE HP from ORAFTI) | 3 g AS |
| Behenyltrimethylammonium chloride | 1.8 g AS |
| Ethyltrimethylammonium methacrylate chloride (SALCARE SC 95 from CIBA) | 1.5 g AS |
| Amodimethicon (BELSIL ADM 6057 E from WACKER) | 1.7 g AS |
| Water qs | 100 g |

The composition has a thick texture and is highly melting on application to wet hair. Its rinsability is good. The wet hair is not charged and it is easy to shape the hair.

EXAMPLE 2

An after-shampoo in accordance with the invention was prepared which has the following composition:

| | |
|---|---|
| Inulin (RAFTILINE HP from ORAFTI) | 5 g AS |
| Ethyltrimethylammonium methacrylate chloride (SALCARE SC 95 from ORAFTI) | 1 g AS |
| Water qs | 100 g |

The treated hair has the same properties as that treated with the composition of Example 1.

EXAMPLE 3

An after-shampoo in accordance with the invention was prepared which has the following composition:

| | |
|---|---|
| Inulin (RAFTILINE HP from ORAFTI) | 1.7 g AS |
| Palmitylamidopropyltrimethylammonium chloride | 1.8 g AS |
| Ethyltrimethylammonium methacrylate chloride (SALCARE SC 95 from CIBA) | 2.3 g AS |
| Avocado oil | 2.5 g |
| Water qs | 100 g |

The treated hair has the same properties as that treated with the composition of Example 1.

EXAMPLE 4

An after-shampoo in accordance with the invention was prepared which has the following composition:

| | |
|---|---|
| Inulin (RAFTILINE HP from ORAFTI) | 15 g AS |
| Palmitylamidopropyltrimethylammonium chloride | 4 g AS |
| Ethyltrimethylammonium methacrylate chloride homopolymer (SALCARE SC 95 from CIBA) | 0.1 g AS |
| Isopropyl myristate | 2 g |
| Water qs | 100 g |

The treated hair has the same properties as that treated with the composition of Example 1.

EXAMPLE 5

An after-shampoo in accordance with the invention was prepared which has the following composition:

| | |
|---|---|
| Inulin (RAFTILINE HP from ORAFTI) | 8 g AS |
| Behenyltrimethylammonium chloride | 2.5 g AS |
| Copolymer of acrylamide and of beta-methacrylyloxyethyltrimethylammonium chloride (ROHAGIT KF 720 from ROHM) | 0.8 g AS |
| Crosslinked divinyldimethicone/dimethicone as a cationic emulsion (DC2-1997 from DOW CORNING) | 1 g AS |
| Water qs | 100 g |

The treated hair has the same properties as that treated with the composition of Example 1.

EXAMPLE 6

An after-shampoo in accordance with the invention was prepared which has the following composition:

| | |
|---|---|
| Inulin (RAFTILINE HP from ORAFTI) | 15 g AS |
| Sodium lauryl ether sulfate containing 2.2 mol of ethylene oxide | 1 g AS |
| Polyquaternium-10 (JR 400 from AMERCHOL) | 1.2 g AS |
| Avocado oil | 8 g |
| Water qs | 100 g |

The treated hair has the same properties as that treated with the composition of Example 1.

The invention claimed is:
1. A cosmetic composition, characterized in that it comprises, in a cosmetically acceptable medium, at least one cationic polymer selected from the group consisting of cellulose ether derivatives comprising quaternary ammonium groups, cationic cellulose derivatives such as cellulose copolymers or cellulose derivatives grafted with a quaternary ammonium water-soluable monomer, cationic polysaccharides, and polyalkyleneimines, and at least one inulin,
wherein the inulin is present in an amount of between 0.01% and 20% and the cationic polymer is present in an amount of between 0.001% and 20% by weight relative to the total weight of the composition.

2. The composition as claimed in claim 1, characterized in that the cationic polymers are chosen from those which contain units comprising primary, secondary, tertiary and/or quaternary amine groups which may either form part of the principal polymer chain, or which may be carried by a side substituent directly linked thereto.

3. The composition as claimed in claim 1, characterized in that said quaternary cellulose ether derivatives are chosen from hydroxyethyl celluloses which have reacted with an epoxide substituted with a trimethylammonium group.

4. The composition as claimed in claim 1, characterized in that said cationic polysaccharides are chosen from guar gums modified with a 2,3-epoxy-propyltrimethylammonium salt.

5. The composition as claimed in claim 1, characterized in that it comprises, in addition, at least one silicone.

6. The composition as claimed in claim 5, characterized in that the silicones are chosen from polyorganosiloxanes insoluble in the composition.

7. The composition as claimed in either of claims 5 and 6, characterized in that the silicones are nonvolatile polyorganosiloxanes chosen from polyalkylsiloxanes, polyarylsiloxanes, polyalkylarylsiloxanes, silicone gums and resins, polyorganosiloxanes modified by organofunctional groups, and mixtures thereof.

8. The composition as claimed in claim 7, characterized in that:
(a) the polyalkylsiloxanes are chosen from:
  polydimethylsiloxanes with trimethylsilyl terminal groups;
  polydimethylsiloxanes with dimethylsilanol terminal groups;
  poly($C_1$-$C_{20}$)alkylsiloxanes;
(b) the polyalkylarylsiloxanes are chosen from:
  polydimethylmethylphenylsiloxanes, polydimethyldiphenylsiloxanes which are linear and/or branched and have a viscosity of between $1\times10^{-5}$ and $5\times10^{-2}$ m$^2$/s at 25° C.;
(c) the silicone gums are chosen from polydiorgano-siloxanes having number-average molecular masses of between 200,000 and 1,000,000, used alone or in the form of a mixture in a solvent;
(d) the resins are chosen from the resins consisting of units:
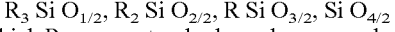
in which R represents a hydrocarbon group having from 1 to 16 carbon atoms or a phenyl group;
(e) the organomodified silicones are chosen from silicones comprising in their structure one or more organofunctional groups attached via a hydrocarbon radical.

9. The composition as claimed in claim 5, characterized in that the silicones are chosen from polyalkylsiloxanes with trimethylsilyl terminal groups, polyalkylsiloxanes with dimethylsilanol terminal groups, polyalkyl-arylsiloxanes, mixtures of two PDMSs consisting of a gum and an oil with different viscosities, mixtures of cyclic silicones and organosiloxanes, and organopolysiloxane resins.

10. The composition as claimed in claim 1, characterized in that it comprises, in addition, at least one agent beneficial to the hair, chosen from esters of $C_1$-$C_{30}$ carboxylic acids and $C_1$-$C_{30}$ mono- or polyhydroxylated alcohols, vegetable, animal, mineral or synthetic oils, waxes, ceramides and pseudoceramides.

11. The composition as claimed in claim 1, characterized in that the inulin is present at a concentration of between 0.01% and 20% by weight relative to the total weight of the composition.

12. The composition as claimed in claim 1, characterized in that the cationic polymer is present at a concentration of between 0.01% and 10% by weight relative to the total weight of the composition.

13. The composition as claimed in claim 5, characterized in that said silicone is present at a concentration of between 0.001% and 20% by weight relative to the total weight of the composition.

14. The composition as claimed in claim 10, characterized in that the agent beneficial to the hair is present at a concentration of between 0.001% and 20% by weight relative to the total weight of the composition.

15. The composition as claimed in claim 1 characterized in that it comprises, in addition, at least one surfactant chosen from anionic, nonionic, amphoteric and cationic surfactants, and mixtures thereof.

16. The composition as claimed in claim 15, characterized in that the surfactant(s) are present at a concentration of between 0.01% and 50% by weight relative to the total weight of the composition.

17. The composition as claimed in claim 1, characterized in that it is provided in the form of a shampoo, an after-shampoo, a composition for permanent waving, straightening, dyeing or bleaching the hair, a rinse-off composition to be applied between the two stages of a permanent waving or hair straightening, or a washing composition for the body.

18. A method for applying a cosmetic composition to keratinous materials comprising applying the composition of claim 1 to a keratinous material and optionally rinsing with water.

19. A method for the manufacture of a cosmetic composition, comprising combining in a cosmetically acceptable medium, at least one cationic polymer selected from the group consisting of cellulose ether derivatives comprising quaternary ammonium groups, cationic cellulose derivatives such as cellulose copolymers or cellulose derivatives grafted with a quaternary ammonium water-soluable monomer, cationic polysaccharides and polyalkyleneimines, and at least one inulin, wherein the inulin is present in an amount of between 0.01% and 20% and the cationic polymer is present in an amount of between 0.001% and 20% by weight relative to the total weight of the composition.

20. The method of claim 18 wherein the keratinous material comprises hair.

21. The method of claim 18 wherein the keratinous material comprises skin, eyelashes, eyebrow, nails or scalp.

22. The composition as claimed in claim 1, characterized in that the inulin is present at a concentration of between 0.05% and 15% by weight relative to the total weight of the composition.

23. The composition as claimed in claim 5, characterized in that the silicone is present at a concentration of between 0.01% and 10% by weight relative to the total weight of the composition.

24. The composition as claimed in claim 10, characterized in that the agent beneficial to the hair is present at a concentration of between 0.01% and 10% by weight relative to the total weight of the composition.

25. The composition as claimed in claim 15, characterized in that the surfactant(s) are present at a concentration of between 0.1% and 40% by weight relative to the total weight of the total weight of the composition.

26. The composition as claimed in claim 15, characterized in that the surfactant(s) are present at a concentration of between 0.5% and 30% by weight, relative to the total weight of the total weight of the composition.

* * * * *